United States Patent
Bragante et al.

(10) Patent No.: US 6,187,975 B1
(45) Date of Patent: *Feb. 13, 2001

(54) PREPARATION PROCESS OF 227

(75) Inventors: Letanzio Bragante, Padua; Paolo Cuzzato, Treviso, both of (IT)

(73) Assignee: Ausimont S.p.A., Milan (IT)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 9 days.

(21) Appl. No.: 09/333,683

(22) Filed: Jun. 16, 1999

(30) Foreign Application Priority Data

Jun. 19, 1998 (IT) ............................... MI98A1407

(51) Int. Cl.⁷ .................................................. C07C 17/08
(52) U.S. Cl. ........................... 570/166; 570/168; 570/169
(58) Field of Search .................................... 570/166, 168, 570/169

(56) References Cited

U.S. PATENT DOCUMENTS

| | | |
|---|---|---|
| 5,345,014 | 9/1994 | Cuzzato . |
| 5,475,169 | 12/1995 | Hopp et al. . |
| 5,563,304 | 10/1996 | Rao et al. . |
| 5,573,654 | 11/1996 | Cheburkov et al. . |
| 5,621,152 | 4/1997 | Jansen . |

FOREIGN PATENT DOCUMENTS

| | | |
|---|---|---|
| 0 039 471 A1 | 11/1981 | (EP) . |
| 0 539 989 A1 | 5/1993 | (EP) . |
| 0 562 509 A1 | 9/1993 | (EP) . |
| 0 634 384 A1 | 1/1995 | (EP) . |
| 0 773206 | 4/1997 | (EP) . |
| WO 92/13817 | 8/1992 | (WO) . |
| WO 96/02483 | 2/1996 | (WO) . |
| 99 06342 | 2/1999 | (WO) . |

*Primary Examiner*—Alan Siegel
(74) *Attorney, Agent, or Firm*—Arent, Fox, Kintner, Plotkin & Kahn

(57) ABSTRACT

Perfluoropropene (PFP) hydrofluorination process in gaseous phase to obtain $CF_3$—$CHF$—$CF_3$ (A-227ea), characterized in that as catalyst fluorinated alumina containing at least 90% by weight of $AlF_3$, is used, the HF/PFP molar ratios range from about 4:1 to 20:1, the hydrofluorination process temperature being in the range 320°–420° C.

9 Claims, No Drawings

PREPARATION PROCESS OF 227

The present invention relates to a process for obtaining $CF_3$—CHF—$CF_3$ (227ea) with high yields and selectivity.

More specifically the present invention relates to a perfluoropropene (PFP) hydrofluorination process in gaseous phase which uses a particular catalyst for obtaining $CF_3$—CHF—$CF_3$ (227ea) with high yields and selectivity, the PFP amount at the end of the reaction being lower than 3% by weight, preferably lower than 0.05% by weight.

More specifically the present invention relates to a process for preparing 227 in the ea form without the presence of 227ca $CF_3$—$CF_2$—$CHF_2$.

It is known that, owing to well known problems of atmospheric ozone layer depletion, the use and production of chlorofluorocarbons (CFC) such as A-11 ($CCl_3F$), A-12 ($CCl_2F_2$), A-113 ($CCl_2FCClF_2$), A-114 ($CClF_2CClF_2$), have been banned or limited since they have at least a chlorine atom in their structure. Compounds not containing chlorine atoms in their molecule such as for instance 32 ($CH_3F$), 125 ($CHF_2CF_3$), 134a ($CF_3CH_2F$), 227 ($CF_3$—CHF—$CF_3$ or $CF_3$—$CF_2$—$CHF_2$), 236 ($CF_3CH_2CF_3$ or $CF_3CFHCF_2H$) etc., up to hydrofluorinated series ends also higher than 4, 5 carbon atoms are therefore requested in their use also in mixtures, as solvents, refrigerants, foaming agents for polymeric resins, extinguishing agents, propellants for aerosol, sterilizing mixtures, etc.

The 227ea synthesis by hydrofluorination with the use of HF, $Cl_2$ and catalysts of the relevant chlorinated compounds is known from the prior art. However the chlorinated precursors are not easily preparable with a good purity degree and yield. Besides for compounds with 3 or more carbon atoms as for 227ea, such preparation is difficult and for the hydrofluorination in gaseous phase is still more problematic, as it requires conditions leading to not very high yields and selectivity. See for instance patent application WO 92/13817 which describes also the 227 synthesis from chlorofluorinated precurosors in gaseous phase obtaining extremely complex hydrochlorofluorinated product mixtures in various ratios by employing HF and $Cl_2$ and $CrO_3$ or $Cr_2O_3/Al_2O_3$ catalyst.

The fluorination in homogeneous liquid phase with HF of the relevant chlorinated precursors with the use for instance of antimony-based catalysts, such as $SbCl_5$ and $SbF_5$, etc., is also described in the prior art. However these hydrofluorinations generally show not high yields and selectivity. Besides there is a catalyst rapid deactivation, due to pitch formation, which must be moreover brought again to the initial oxidation state for instance by using chlorine.

It is to be noticed that the antimony compound use is difficult for its toxicity. See patent application WO 96/02483.

Other known processes for the 227 synthesis relate to the reduction with hydrogen on catalysts or in gaseous phase of the relevant chlorinated precursor. The yields and selectivities of these processes are not high; therefore the reactants recycle is necessary: this operation can be difficult when the separation is not easy. Besides the catalyst has a not long duration. Besides the precursors are not easy to be prepared. See EP 539,989, EP 562,509, EP 39,471.

The synthesis by summing HF to perfluoropropene is also known, by using a slightly basic tertiary amine to promote the sum reaction. However the yields and selectivities are unsatisfactory and besides there is the drawback of the aminic reactant consumption. See EP 634,384.

The synthesis by summing the HF to pentafluoroproene on $Cr_2O_3$ catalyst is also known. Also in this case the yields and selectivities ar not good. Besides this process relates to the preparation of 236, which can be used as precursor of 227. See U.S. Pat. No. 5,563,304.

The 227ea synthesis starting from perfluoroisobutene in a basic aqueous alcoholic medium for the presence of triethylamine is also described. 227ea is obtained only in a very low percentage. Besides, it is to be noticed that the starting perfluoroisobutene is commonly considered a very toxic compound. See U.S. Pat. No. 5,573,654.

There are also other patents on the 227 purification from the unreacted perfluoropropene. See for instance U.S. Pat. No. 5,475,169, which uses for the 227ea purification from the unreacted PFP a reaction with NaOH, KOH and alcohols. U.S. Pat. No. 5,621,152 leads to the elimination also of very reduced amounts, 50 ppm, of perfluoropropene by passing the mixture on alumina.

The need was felt to have available an industrial process for preparing 227ea with high yields and selectivity, without leading to the contemporaneous presence of 227ca, wherein the unreacted PFP amount or, in case, of other olefin is very reduced, in the range of 3% by weight.

An object of the present invention is a perfluoropropene (PFP) hydrofluorination process in gaseous; phase to obtain $CF_3$—CHF—$CF_3$ (227ea), characterized in that, as catalyst, fluorinated alumina containing at least 90% by weight, preferably 95W of $AlF_3$, preferably in gamma form, optionally containing a compound of trivalent chromium under oxide, oxyfluoride or fluoride form, or mixtures threof, is used, the chromium amount as metal being in the range 1–15% by weight, preferably 2–10% by weight, the HF/PFP molar ratios range from about 4:1 to 20:1, preferably from 6:1 to 14:1, more preferably from 8:1 to 11:1, the hydrofluorination process temperature being in the range 320°–420° C., preferably 340–°400° C., still more prefrably 340°–370° C., the feeding gas pressure being in the range 1–30 absolute atm, preferably 2–10, still more preferably 5–10.

Preferably the PFP amount at the end of the reaction being lower than 3% by weight, preferably lower than 0.05% by weight.

The contact time ranges from 10 to 50 sec, preferably from 20 to 30 sec.

The catalyst used in the present invention is obtainable for example by the process described in previous patents in the name of the Applicant. See for isntaiice U.S. Pat. No. 5,345,014 herin incorporated by reference. Tests carried out: by the Applicant on the final catalyst of U.S. Pat. No. '014 have shown that after the activation or regeneration phase the chromium is present in the form of oxide, oxyfluoride and fluoride. The oxide and fluoride amounts, by weight, are generally of the same order.

It is to be noted that by the invention process 227 in the ea form is obtained without the presence of 227ca ($CF_3$—$CF_2$—$CHF_2$). This represents an advantage from the industrial point of view since the two 227 isomers are difficult: to be separated with the usual separation methods, such as distillation, since they have very close boiling temperatures.

With the invention process high yields of 227ea higher than 95% by weight, preferably higher than 97% by weight, still more preferably higher than 99% are obtained., by operating in the preferred range of the above mentioned process variables.

It has been surprisingly and unexpectedly found that the invention catalyst deactivation rate is very low: the PFP reactant conversion does not lower more than 0.05 moles/h preferably 0.02 moles/h, more preferably 0.01 moles/h for running times in the range of 200 h or higher. From the industrial point of view this is an advantage since the catalyst regeneration is not frequent, obtaining substantially constant PFP conversions.

Besides it has been surprisingly and unexpectedly found that with the invention process an amount of perfluoroisobutene by-product lower than 0.1 ppb is obtained.

Besides the invention process by giving very high PFP conversions does not require the unreacted product recycle, remarkably simplifying the process from the industrial point of view.

The reaction mixture can be purified from the small PFP amounts or from other olefins formed in the process by using processes known in the art, for instance U.S. Pat. No. 5,475,169 and U.S. Pat. No. 5,621,152 herein incorporated by reference.

The catalyst used for the hydrofluorination in gaseous phase of the present invention is in a form suitable for the use in fluidized bed or fixed bed reactor. The fluidized bed reactor is preferred for its better homogeneity and thermal exchange features.

Another important feature of the present invention is the perfluoropropene use as starting compound, such compound is easily available in industrial scale with respect to other fluorinated precursors used in the art.

The present invention will now be better illustrated by the following examples, which have only an indicative but not limitative purpose of the scope of the invention itself.

EXAMPLES

Charcterization

The compounds are analyzed by the IR, FT-NMR and GC-MSD techniques; the IR analysis of the product in gaseous phase confirms the presence of the band at 3.000 cm$^{-1}$ due to the C—H bond and the band disappearance at 1.780 cm$^{-1}$ of the $CF_2$=$CFCF_3$ double bond, the FT-NMR analysis confirms the presence of only the isomer $CF_3CFHCF_3$ (227ea) and the GC-MSD analysis confirms a ≧99.9% selectivity; the perfluoroisobutene presence is shown by the ECD electron capture analysis.

Example 1 comparative

Perfluoropropene ($C_3F_6$) pure product ≧99.99% is allowed to react with HF in a monel tubular reactor having a 9.3 mm diameter containing 8.1 g of a catalyst formed by $AlF_3$ having a granulometry in the range 150–300$\mu$ impregnated with aqueous solution of $FeCl_3$, $NiCl_2$ and $CrCl_3$ in such amount as to achieve a final concentration by weight in the catalyst of said metals of 1.25%, 0.5%, 0.5% respectively. The reactants are fed as gas in the following ratios:
HF=63 mmole/h
PFP=62 mmole/h
inert gas (helium)=26 mmole/h
at the 1.1 atm pressure at the temperature of 360° C.

The reaction products are passed through a water or soda washing system to remove the unreacted HF and subsequently analyzed by gaschormatography.

The test result is reported in Table 1.

TABLE 1

| TEMPERATURE ° C. | 227ea % by wt. | PFP % by wt. | SELECTIVITY % by wt. |
|---|---|---|---|
| 360 | 1.87 | 97.88 | 88 |

The perfluoroisobutene amount is of 20 ppm.

Such example shows the poor reaction yield and the low selectivity using this catalyst cleary not very suitable for this reaction.

Example 2

(comparative)

Perfluoropropene ($C_3F_6$) pure product ≧99.99% is allowed to react with HF in a monel tubular reactor having a 9.3 mm diameter containing 9.90 g of a catalyst prepared by impregnating $AlF_3$ of Example 1 with a $CrCl_3$ aqueous solution in such amount as to obtain a final Cr concentration in the catalyst equal to 6.5% by weight.

The reactants are fed as gas in the following ratios:
HF 2.36 g/h=118 mmole/h
PFP=62 mmole/h
inert gas (helium) 47 mmole/h
at the 1.1 atm pressure and at different temperatures.

The test results at the different temperatures are reported in Table 2.

TABLE 2

| TEMPERATURE ° C. | A 227ea % by wt. | PFP % by wt. |
|---|---|---|
| 240 | 37.98 | 61.99 |
| 250 | 68.55 | 31.34 |
| 270 | 89.02 | 10.05 |
| 290 | 97.39 | 2.89 |
| 310 | 99.26 | 0.67 |
| 340 | 99.48 | 0.28 |
| 360 | 99.42 | 0.52 |

The perfluoroisobutene amount is of 20 ppm in each test carried out at different temperatures.

Example 3

(comparative)

Perfluoropropene ($C_3F_6$) pure product ≧99,99% is allowed to react with HF in a monel tubular reactor having a 9.3 mm diameter containing 8.0 g of a catalyst formed by only AlF3 as defined in Example 1. The reactants are fed as gas in the following ratios:
HF 2.36 g/h=118 mmole/h
PPP=62 mmole/h
inert gas (helium)=47 mmole/h at the 1.1 atm pressure and at different temperatures.

The reaction products are treated as in Example L.

The test results at the different temperatures are reported in Table 3.

TABLE 3

| TEMPERATURE ° C. | 227ea % by wt. | PFP % by wt. |
|---|---|---|
| 310 | 84.47 | 15.52 |
| 340 | 98.56 | 1.04 |
| 360 | 99.39 | 0.42 |

Also for each of these tests the presence of 20 ppm of perfluoroisobutene has been noticed.

Example 4

In an Inconel reactor having a 5.00 cm diameter, 1200 g of a catalyst prepared according to the procedure of Example 2 but containing 8.0% by weight of chromium are introduced. The reactants are fed to the reactor at the pressure of 3.5 atm in the following ratios:
HF 300 g/h=15.00 mole/h
PFP 36 L/h at 20° C. 1.497 mole/h
The reaction products are treated as in Example 1. The test results at the different temperatures are recorded in Table 4.

TABLE 4

| TEMPERATURE ° C. | 227ea % by wt. | SELECTIVITY % by wt. |
|---|---|---|
| 300 | 93.85 | 99.95 |
| 300 | 93.88 | 99.92 |
| 320 | 97.22 | 99.98 |
| 340 | 98.48 | 99.98 |
| 360 | 98.97 | 99.86 |
| 360 | 99.60 | 99.60 |
| 380 | 99.19 | 99.73 |
| 380 | 99.85 | 99.87 |

The balance to 100 is for the most part. PFP. The perfluoroisobutene amount for each test is lower than 0.1 ppb.

Example 5

In an Inconel reactor having a 5.00 cm. diameter 1200 g of the catalyst of Example 4 are introduced. The reactants are fed to the reactor, at the pressure of 7.0 atm in the following ratios:
HF 300 g/h=15.00 mole/h
PFP 36 L/h at 20° C.=1.497 mole/h The reaction products are treated as in Example 1.
The test results at the different temperatures are reported in Table 5.

TABLE 5

| TEMPERATURE ° C. | 227ea % by wt. | SELECTIVITY % by wt. |
|---|---|---|
| 320 | 97.73 | 99.95 |
| 340 | 99.09 | 99.95 |
| 360 | 99.47 | 99.93 |

The balance to 100 is for the most part PFP. The perfluoroisobutene amount for each test is lower than 0.1 ppb.

These examples show how high pressures rather than the room pressure are to be preferred to carry out this synthesis with higher reaction yield.

Example 6

In an Inconel reactor having a 5.00 cm. diameter, 1200 g of the catalyst of Example 4 are introduced. At the pressure of 7.0 atm and at different temperatures, the reactants are fed in different ratios so as to achieve different molar ratios among each other, thus achieving different τ stay times (in sec) in the reactor. The used catalyst shows different deactivation rates expressed as % mole/h.

The reaction products are treated as in Example 1. The test results at the differnt temperatures are reported in Table 6.

TABLE 6

| TEMPERATURE ° C. | mol. ratio | τ sec. | 227ea % by wt | SELECTIVITY % by wt. | DEACTIVATION % mole/h |
|---|---|---|---|---|---|
| 320 | 10.2 | 11.4 | 85.73 | — | −0.176 |
| 340 | 10.0 | 27.3 | 99.32 | 99.9 | −0.0032 |
| 360 | 10.0 | 26.7 | 99.45 | 99.7 | −0.0004 |
| 360 | 20.0 | 27.3 | 98.93 | 99.58 | −0.0091 |
| 360 | 20.0 | 27.3 | 98.80 | 99.75 | −0.0072 |
| 360 | 6.7 | 24.9 | 98.85 | 99.98 | −0.0137 |

The balance to 100 is for the most part PFP. This test shows how temperature, reaction yield, used molar ratios allow to reduce to the minimum the deactivation rate of the used catalyst. This allows to less frequently regenerate the catalyst and at the same time to obtain a product which only needs distillation from HF, washing and distillation o:E the possible unreacted PFP.

In each test the perfluoroisobutene amount is lower than 0.1 ppb.

Example 7

In an Inconel reactor having a 5.00 cm diameter, 90C g of an AlF$_3$ catalyst as in Example 3 are introduced.

At the pressure of 7.0 atm and at different temperatures, the reactants are fed in various ratios so as to achieve different molar ratios among each other, thus achieving different τ stay times (in sec) in the reactor. The used catalyst shows different deactivation rates expressed as % mole/h.

The reaction products are treated as in Example 1. The test results at the different temperatures are reported in Table 7.

TABLE 7

| TEMPERATURE ° C. | mol. ratio | τ sec. | 227ea % by wt. | SELECTIVITY % by wt. | DEACTIVATION % mole/h |
|---|---|---|---|---|---|
| 400 | 10.0 | 49.3 | 98.75 | 99.75 | nd |
| 400 | 10.0 | 24.6 | 98.38 | 99.85 | −0.0093 |
| 400 | 10.0 | 36.9 | 97.55 | 99.85 | −0.0031 |
| 380 | 10.0 | 35.8 | 98.67 | 99.80 | −0.0040 |
| 380 | 10.0 | 35.8 | 98.70 | 99.85 | −0.0066 |
| 360 | 10.0 | 26.2 | 96.56 | 99.85 | −0.0057 |

The balance to 100 is for the most part PFP. In each test the determined perfluoroisobutene amount is, lower than 0.1 ppb.

This test shows how temperature, reaction yield, used molar ratios allow to reduce to the minimum the deactivation rate of the used catalyst.

What is claimed is:

1. A process for hydroflourinating perfluoropropene (PFP) in gaseous phase to obtain $CF_3$—CHF—$CF_3$ (227ea), characterized by the presence of a fluorinated alumina catalyst containing at least 90% by weight of AlF$_3$, optionally containing a compound of trivalent chromium oxide, oxyfluoride or fluoride:
   a HF/PFP molar ratio range from about 4:1 to 20:1, the hydrofluorination process temperature being in the range 320–420° C., the feeding gas pressure being in the range from 1 to 30 absolute atm.

2. The process according to claim 1 wherein the catalyst is fluorinated alumina containing 95% by weight of ALF$_3$ in gama form.

3. The process according to claim 1 wherein the HF/PFP molar ratio range is from 6:1 to 14:1.

4. The process according to claim 1 wherein the hydrofluorination process temperature is in the range of 340–400° C.

5. The process according to claim 1 wherein the chromium as metal in the catalyst is present in amounts comprised between 1 and 15% by wt.

6. The process according to claim 5 wherein the chromium is comprised between 2 and 10% by weight.

7. The process according to claim 1 wherein the contact time ranges from 10 to 50 sec.

8. The process according to claim 1, wherein the catalyst is a form suitable for the use in a fluidized bed or a fixed bed reactor.

9. The process according to claim 1 wherein the PFP amount at the end of the reaction is less than 3% by weight.

* * * * *